United States Patent [19]

Hoffmann et al.

[11] 4,314,843
[45] Feb. 9, 1982

[54] 1-BENZOYL-3-HYDROXY-6(1H)-PYRIDAZI-NONES EMPLOYED AS PLANT GROWTH REGULATORS

[75] Inventors: Otto L. Hoffmann, Wilmington, Del.; Natu R. Patel, Overland Park, Kans.

[73] Assignee: Gulf Oil Corporation, Pittsburgh, Pa.

[21] Appl. No.: 194,502

[22] Filed: Oct. 6, 1980

Related U.S. Application Data

[62] Division of Ser. No. 124,991, Mar. 13, 1980, Pat. No. 4,256,884.

[51] Int. Cl.³ .............................................. A01N 43/58
[52] U.S. Cl. ...................................................... 71/92
[58] Field of Search ............................................. 71/92

[56] References Cited

U.S. PATENT DOCUMENTS 2,614,917 10/1952 Zukel et al. .............................. 71/92
3,867,126 2/1975 Kupelian .................................. 71/92
4,045,207 8/1977 Convent ................................... 71/92

*Primary Examiner*—Catherine L. Mills
*Attorney, Agent, or Firm*—Deane E. Keith; Forrest D. Stine; Carl A. Cline

[57] ABSTRACT

A novel class of growth regulator compounds of the structural formula

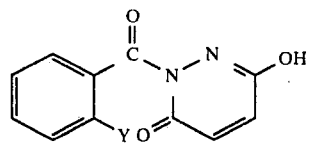

is disclosed, in which Y is —COOH or an agriculturally acceptable salt thereof, —COOR, —CH$_2$OH, —CHO, —R, —OR or halogen and R is C$_1$ to C$_4$ alkyl or alkenyl.

15 Claims, No Drawings

1-BENZOYL-3-HYDROXY-6(1H)-PYRIDAZINONES EMPLOYED AS PLANT GROWTH REGULATORS

This is a division of application Ser. No. 124,991, filed Mar. 13, 1980, now U.S. Pat. No. 4,256,884.

DESCRIPTION OF THE INVENTION

The use of 1,2-dihydro-3,6-pyridazinedione, commonly called maleic hydrazide, as a plant growth regulator and inhibitor is widespread and has been responsible for significant improvements in the production of certain specific agricultural crops. Many derivatives of this active substance have also been known for some time, none of which has shown any substantial improvement or useful difference in growth regulating activity, in comparison with the parent compound. It has been known, for example that the benzoyl derivative, 1-benzoyl-3-hydroxy-6(1H)-pyridazinone, having the structural formula

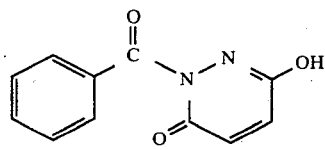

has growth inhibiting activity approximately equal to maleic hydrazide, as measured by inhibition of bud growth on soybeans. (*Canadian J. Biochem. and Physiol.* v. 40 p. 1159–1165, September 1962, also U.S. Pat. No. 2,614,917.) When applied to soybean plants which are in the process of setting pods, or on which pods are set, this compound causes the pods to shrink, turn brown and drop.

We have discovered a novel class of compounds that differs from the aforementioned compound only by the presence of a single substituent group, which possesses growth regulating activity of a distinctly different type, so that these compounds may be used, for example, to increase the setting and filling of pods on soybeans, as well as for other purposes, such as selective post-emergent control of wild oats.

Briefly, the novel growth regulators of the present invention are compounds having the structural formula

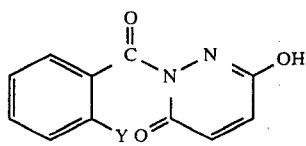

in which Y is —COOH or an agriculturally acceptable salt thereof, —COOR, —CH$_2$OH, —CHO, —R, —OR or halogen and R is C$_1$ to C$_4$ alkyl or alkenyl.

SYNTHESIS OF THE NOVEL GROWTH REGULATORS

The growth regulator compounds are readily synthesized from commercially available intermediates or by reaction of maleic hydrazide with ortho-substituted benzoic acids which are easily made by conventional methods. An illustrative procedure appears below.

SYNTHESIS OF 1-(2-CARBOMETHOXYBENZOYL)-3-HYDROXY-6(1H)-pyridazinone

Into a 100 ml round-bottomed flask fitted with a stirrer and reflux condenser there was charged 10.8 g (0.06 mole) of 2-carbomethoxybenzoic acid and 50 ml of chloroform. There was then added 7.8 g (0.066 mole) of SOCl$_2$, followed by refluxing for 2 hr. The chloroform was then removed by distillation, followed by addition of 50 ml. of dimethoxyethane, 4.7 g (0.06 mole) of pyridine and 6.7 g (0.06 mole) of maleic hydrazide. The mixture was allowed to stir over night. The resulting reaction mixture was filtered to remove solids. Then the product was precipitated from the filtrate by addition of water and was recovered as a solid by filtration. The solid material was washed with hexane-ether solvent mixture and was filtered and dried. The yield was 6.6 g, m.p. 144°–145° C. Infrared and nuclear magnetic resonance spectra were consistent with the structure of the compound as named above.

USE OF THE GROWTH REGULATORS

By application of an effective amount of the growth regulators, either pre- or post-emergently, various effects on young plants become apparent. These effects may be demonstrated by means of the following illustrative procedures.

PRE-EMERGENT APPLICATION

Disposable paper trays about 2½ inches deep which were filled with soil were sprayed with aqueous spray mixtures at a rate of 10 lb. of active chemical per acre of sprayed area, then were seeded with 6 species of plant seeds and were covered with about ¼ inch of soil. The spray mixtures were prepared by dissolving the proper amount of growth regulant compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule.

| DEGREE OF EFFECT |
| --- |
| 0 = no effect |
| 1 = slight effect, plants recovered |
| 2 = moderate effect, injury to 26 to 75 percent |
| 3 = severe effect, injury to 76 to 99 percent of foliage |
| 4 = miximum effect (all plants died) |

POST-EMERGENT APPLICATION

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulator.

Plant injury was again rated according to the schedule disclosed above.

Observations of growth regulator effects in both pre- and post-emergent tests were observed and recorded as follows:

| Effect | Abbreviation in Tables |
|---|---|
| Formative effect on new growth | F |
| Epinasty | E |
| Growth reduction | G |
| Necrosis | N |
| Non-emergence | K |
| Chlorosis | C |

In the table below there are tabulated various observations of pre- and post-emergent herbicidal and growth regulator effects of the compounds disclosed above.

ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants were observed within approximately three weeks after spray treatment and the results are tabulated below. The severity of growth regulatory effect on the plants was estimated on a scale of 0 to 10 and is also recorded in the following table:

TABLE I

GROWTH REGULANT EFFECTS OF COMPOUNDS OF THE FORMULA

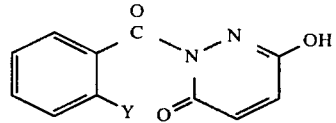

| Compound No. | Y | M.P. °C. | Pre-emergent Effects | | | | | | Comments |
|---|---|---|---|---|---|---|---|---|---|
| | | | Digitaria sanguinalis | Celosia plumosa | Bromus inermis | Setaria italica | Raphanus sativus | Beta vulgaris | |
| 3712 | —COOCH₃ | 144–145 | G3F2 | G2 | K3G3 | G3 | G2 | G2F1 | |
| 4082 | —COOC₂H₅ | 117–119 | 0 | G1 | 0 | G1 | G1 | G1 | |
| 4139 | —COOH | >200 dec. | F1G1 | F2G2 | F3G3 | F3G3 | F1G1 | N2G2 | Promotes axillary growth |
| 4237 | —CH₃ | 162–164 | 0 | F1 | 0 | F1 | 0 | 0 | |
| 4238 | —Cl | >210 dec. | G1 | G2 | G1 | G3 | G3 | G2 | |
| 4240 | —COOCH₂CH₂CH₃ | 102–105 | G1 | G2 | G2 | G3 | G2 | G1 | |
| 4282 | —OCH₃ | 160–170 | G2 | G2 | G2 | G3 | G2 | G1 | |

| Compound No. | Y | M.P. °C. | Post-emergent Effects | | | | | | Comments |
|---|---|---|---|---|---|---|---|---|---|
| | | | Setaria italica | Medicago sativa | Avena sativa | Raphanus sativus | Beta vulgaris | Lycopersicum esculentum | |
| 3712 | —COOCH₃ | 144–145 | G2 | G2 | G3F1 | G2 | F2G1 | N1 | |
| 4082 | —COOC₂H₅ | 117–119 | 0 | 0 | 0 | 0 | 0 | 0 | |
| 4139 | —COOH | >200 dec. | G1 | F1G1 | G3F1 | 0 | F1 | F1 | Promotes axillary growth |
| 4237 | —CH₃ | 162–164 | N1G1 | N1 | G3 | N1 | N1 | F1 | |
| 4238 | —Cl | >210 dec. | G1 | 0 | G1 | 0 | F1 | 0 | |
| 4240 | —COOCH₂CH₂CH₃ | 102–105 | G1 | G1 | — | G1 | N1G1 | F2G1 | |
| 4282 | —OCH₃ | 160–170 | G1 | 0 | — | 0 | 0 | F1G1 | |

The use of many of the growth regulator compounds may be demonstrated by treatment of soybeans (Soja max) to increase the number of seed pods and by treating tomato plants (Lycopersicum esculentum) to increase fruit set. In an illustrative experiment, Soja max (Evans variety) and Lycopersicum esculentum (Tiny Tim variety) were grown in 4-inch pots (one plant per pot) filled with greenhouse potting soil (2 parts good top soil, 1½ parts builders' sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of actone, adding 2 ml. of a solvent-emulsifier mixture consisting of 60 wt. percent of a commercial polyoxyethylated vegetable oil emulsifier (96 wt. percent active ingredient, Emulphor El-719), 20 wt. percent xylene and 20 wt. percent deodorized kerosene, then bringing total volume up to 80 ml by addition of a 0.156 wt. percent aqueous solution of liquid non-

TABLE II

GROWTH REGULATING EFFECTS ON TWO SPECIES

| Comp'd No. | Rate oz/A | Soja max | | Lycopersicum esculentum | |
|---|---|---|---|---|---|
| | | Pod Count[1] Percent in Comparison to Untreated Plants | Severity of Growth Regulating Effect[2] | Fruit Count[1] Percent in Comparison to Untreated Plants | Severity of Growth Regulating Effect[2] |
| 44082 | 16 | 23[3] | 1.5 | 64 | 0 |
| | 4 | 77[4] | 1 | 86 | 0 |
| | 1 | 100[5] | 1 | 150 | 0 |
| 44139 | 16 | 150 | 0.5 | 107 | 0 |
| | 4 | 100 | 0 | 129 | 0 |
| | 1 | 91 | 0 | 107 | 0 |
| 43712 | 16 | 64[3] | 1 | 0 | 1 |
| | 4 | 96[3] | 0 | 109 | 0 |
| | 1 | 114 | 0 | 150 | 0 |
| 44237 | 16 | 41[3] | 1 | 0 | 1 |
| | 4 | 118[3] | 0 | 27 | 0 |
| | 1 | 118 | 0 | 136 | 0 |
| 44238 | 16 | 68[3] | 0.5 | 0 | 1 |
| | 4 | 145[3] | 0 | 177 | 0 |
| | 1 | 105 | 0 | 123 | 0 |
| 44239 | 16 | 23[3] | 1.5 | 0 | 1 |
| | 4 | 96[3] | 0.5 | 0 | 0 |
| | 1 | 132 | 0 | 14 | 0 |
| 44240 | 16 | 27[3] | 1 | 0 | 0.5 |
| | 4 | 82[3] | 0 | 95 | 0 |
| | 1 | 96 | 0 | 123 | 0 |
| 44282 | 16 | 55[3] | 0.5 | 14 | 0.5 |
| | 4 | 100[3] | 0 | 95 | 0 |

TABLE II-continued

| | | GROWTH REGULATING EFFECTS ON TWO SPECIES | | | |
|---|---|---|---|---|---|
| | | Soja max | | Lycopersicum esculentum | |
| Comp'd No. | Rate oz/A | Pod Count[1] Percent in Comparison to Untreated Plants | Severity of Growth Regulating Effect[2] | Fruit Count[1] Percent in Comparison to Untreated Plants | Severity of Growth Regulating Effect[2] |
| | 1 | 141 | 0 | 136 | 0 |

[1]Checks = 100
[2]Greenhouse rating on scale of 0, no effect; 10, total kill.
[3]Axillary growth; aborting pods.
[4]Pods without beans.
[5]More buds.

The information presented in tabular form herein will enable a worker in the art to make a selection from among the growth regulator compounds of the invention and to make some judgment with regard to application rates, depending upon the effect which is desired. It may be seen, for example, that total kills of some species of vegetation may occur at application rates as high as 5 to 10 lb. per acre, whereas beneficial effects may be observed on living plants at application rates of 1 lb. per acre or less.

The growth regulator compounds are usually formulated as 0.1 to 95 weight percent active ingredient in combination with a surface active agent and one or more inert carriers or diluents, as in emulsifiable formulations, granules and dust formulations, in accordance with established practice in the art. An aqueous spray is usually prepared by mixing a wettable powder or emulsifiable concentrate formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalene-sulfonates, alkylbenzenesulfonates, alkyl sulfates and nonionic surfactants such as products of condensation of ethylene oxide with alkylphenols.

Emulsifiable concentrates of the growth regulator compounds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the growth regulators are seldom applied without the presence of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a nonphytotoxic solvent, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formation comprises the growth regulator compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation.

We claim:

1. The method of regulating plant growth comprising applying to plants an effective amount of a compound having the structural formula

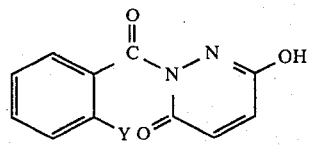

in which Y is —COOH or an agriculturally acceptable salt thereof, —COOR, —CH$_2$OH, —CHO, or —OR, and R is C$_1$ to C$_4$ alkyl or alkenyl.

2. A plant growth-regulating composition comprising from 0.1 to 95 weight percent of a compound having the structural formula

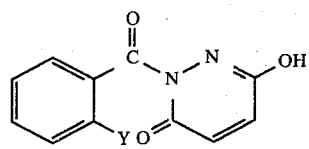

in which Y is —COOH or an agriculturally acceptable salt thereof, —COOR, —CH$_2$OH, —CHO, or —OR, and R is C$_1$ to C$_4$ alkyl or alkenyl, in combination with a surface active agent and an inert carrier.

3. The method of increasing fruit set on agricultural crop plants comprising applying to the plants an effective amount of a compound having the structural formula

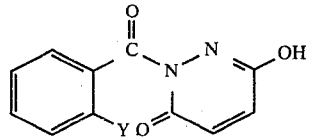

in which Y is —COOH or an agriculturally acceptable salt thereof, —COOR, —CH$_2$OH, —CHO, or —OR, and R is C$_1$ to C$_4$ alkyl or alkenyl.

4. The method of claim 3 in which the crop plants are of the species *Soja max*.

5. The method of claim 3 in which the crop plants are of the species *Lycopersicum esculentum*.

6. The method as specified in claim 1 in which Y is —COOCH$_3$.

7. The method as specified in claim 1 in which Y is —COOC$_2$H$_5$.

8. The method as specified in claim 1 in which Y is —COOH or an agriculturally acceptable salt thereof.

9. The method as specified in claim 1 in which Y is —COOCH$_2$CH$_2$CH$_3$.

10. The method as specified in claim 1 in which Y is —OCH$_3$.

11. The method as specified in claim 3 in which Y is COOCH$_3$.

12. The method as specified in claim 3 in which Y is —COOC$_2$H$_5$.

13. The method as specified in claim 3 in which Y is —COOH or an agriculturally acceptable salt thereof.

14. The method as specified in claim 3 in which Y is —COOCH$_2$CH$_2$CH$_3$.

15. The method as specified in claim 3 in which Y is —OCH$_3$.

* * * * *